(12) United States Patent
Hannan et al.

(10) Patent No.: US 9,119,727 B2
(45) Date of Patent: Sep. 1, 2015

(54) POUCH FOR COLLECTING LIQUID EXCRETIONS

(75) Inventors: John Francis Hannan, Enniscrone (IE); Claus Dallerup Rasmussen, Vaerlose (DK); Jakub Zygmunt Goczkowski, Copenhagen NV (DK)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 13/988,235

(22) PCT Filed: Nov. 4, 2011

(86) PCT No.: PCT/EP2011/069386
§ 371 (c)(1),
(2), (4) Date: Jun. 25, 2013

(87) PCT Pub. No.: WO2012/069299
PCT Pub. Date: May 31, 2012

(65) Prior Publication Data
US 2014/0163497 A1    Jun. 12, 2014

(30) Foreign Application Priority Data
Nov. 23, 2010   (EP) ..................................... 10192174

(51) Int. Cl.
*A61F 5/44*     (2006.01)
*A61F 5/443*    (2006.01)
*A61F 5/445*    (2006.01)

(52) U.S. Cl.
CPC .............. *A61F 5/443* (2013.01); *A61F 5/4405* (2013.01); *A61F 5/445* (2013.01); *A61F 5/4407* (2013.01); *Y10T 156/10* (2015.01)

(58) Field of Classification Search
USPC ......................................................... 604/344
See application file for complete search history.

(56) References Cited

U.S. PATENT DOCUMENTS 3,189,252 A * 6/1965 Miller .............................. 383/57
4,084,590 A * 4/1978 Caraway et al. .............. 604/335
4,300,560 A   11/1981 Steer et al.
4,519,797 A * 5/1985 Hall ............................... 604/332

(Continued)

FOREIGN PATENT DOCUMENTS

EP          1749507       2/2007
JP        2003126143    * 5/2003   ................ A61F 5/44

OTHER PUBLICATIONS

International Search Report and Written Opinion of the International Search Authority issued Feb. 28, 2012 in connection with PCT/EP2011/060386.

*Primary Examiner* — Tatyana Zalukaeva
*Assistant Examiner* — Guy K Townsend
(74) *Attorney, Agent, or Firm* — Levenfeld Pearlstein, LLC

(57) ABSTRACT

The present invention concerns a pouch for collecting liquid excretions for collecting liquid human waste, said pouch comprising a first and second wall sealed together along their periphery defining an inlet top portion and a bottom portion defining a collection chamber, an inlet opening provided in the top portion of the first wall, and an anti-reflux film provided in the top portion between said first and second walls, wherein the anti-reflux film is sealed along its lower periphery to the first wall by an anti-reflux seal across the first wall, and wherein a plurality of spot welds are provided above the anti-reflux seal and wherein a plurality of slits are provided in the anti-reflux film between the anti-reflux seal and the spot welds.

24 Claims, 3 Drawing Sheets

(56) References Cited

U.S. PATENT DOCUMENTS

| | | | |
|---|---|---|---|
| 4,533,354 A * | 8/1985 | Jensen | 604/323 |
| 4,604,095 A | 8/1986 | Samuelsen | |
| 4,654,037 A * | 3/1987 | Fenton | 604/334 |
| 4,723,944 A * | 2/1988 | Jensen | 604/323 |
| 5,250,042 A * | 10/1993 | Torgalkar et al. | 604/333 |
| 6,712,800 B2 * | 3/2004 | Kanbara | 604/333 |
| 7,090,664 B2 * | 8/2006 | Holter | 604/332 |
| 7,214,217 B2 * | 5/2007 | Pedersen et al. | 604/333 |
| 7,476,220 B2 * | 1/2009 | Lillegaard | 604/342 |
| 7,517,339 B2 * | 4/2009 | Pedersen et al. | 604/345 |
| 7,604,622 B2 * | 10/2009 | Pedersen et al. | 604/333 |
| 8,298,201 B2 * | 10/2012 | Albrectsen | 604/333 |
| 8,449,511 B2 * | 5/2013 | Andersen et al. | 604/332 |
| 8,764,716 B2 * | 7/2014 | Christensen et al. | 604/328 |
| 2003/0014023 A1 * | 1/2003 | Kanbara | 604/333 |
| 2009/0082743 A1 * | 3/2009 | Buglino et al. | 604/335 |
| 2009/0163883 A1 * | 6/2009 | Christensen et al. | 604/328 |
| 2011/0190718 A1 * | 8/2011 | Wheaton et al. | 604/332 |
| 2013/0053802 A1 * | 2/2013 | Maidl et al. | 604/332 |
| 2014/0005619 A1 * | 1/2014 | Andersen et al. | 604/344 |
| 2014/0163497 A1 * | 6/2014 | Hannan et al. | 604/344 |

* cited by examiner

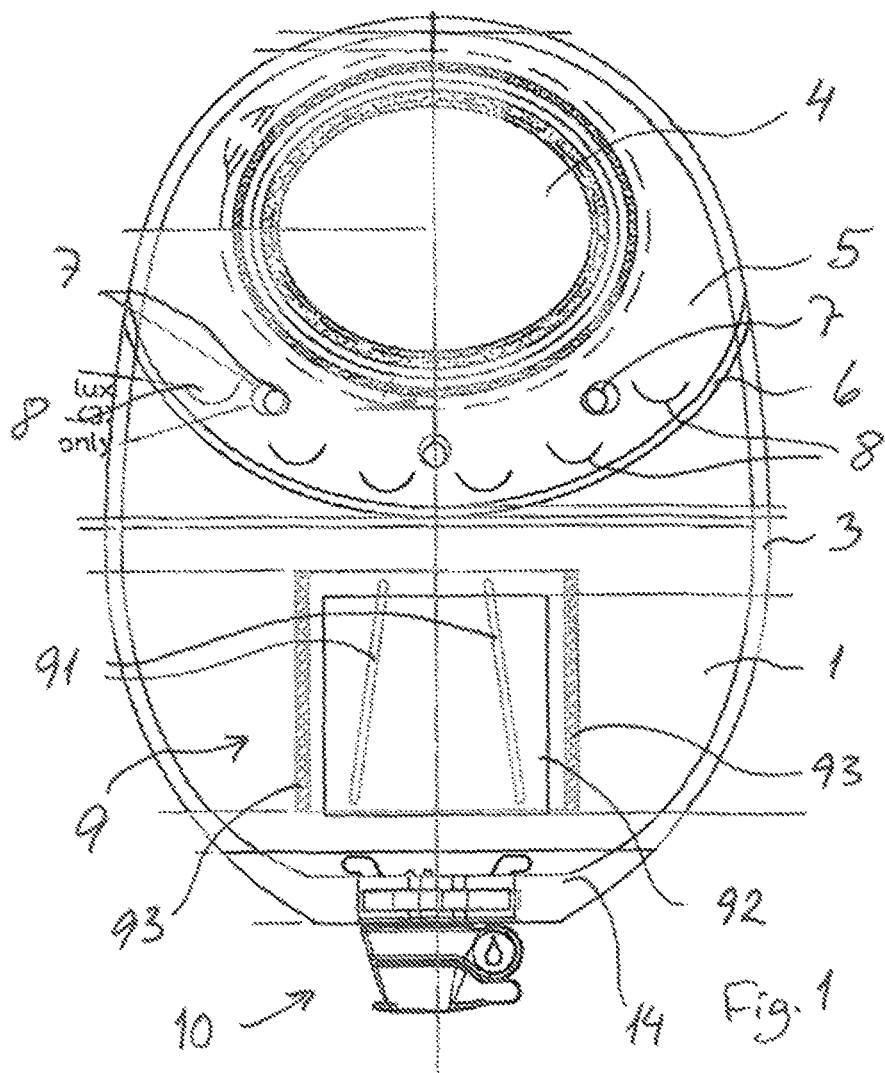
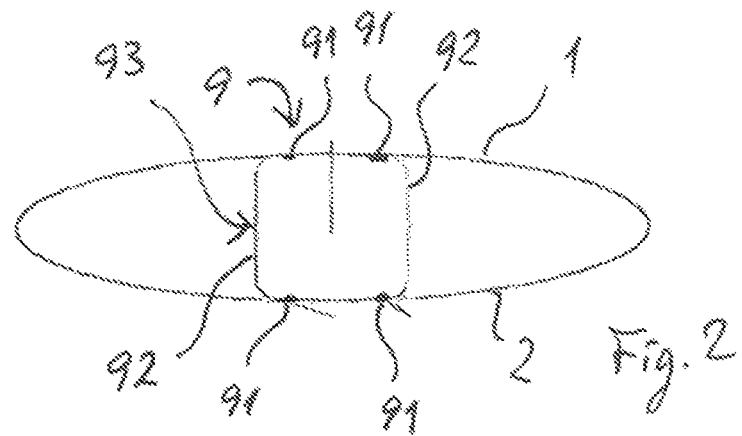

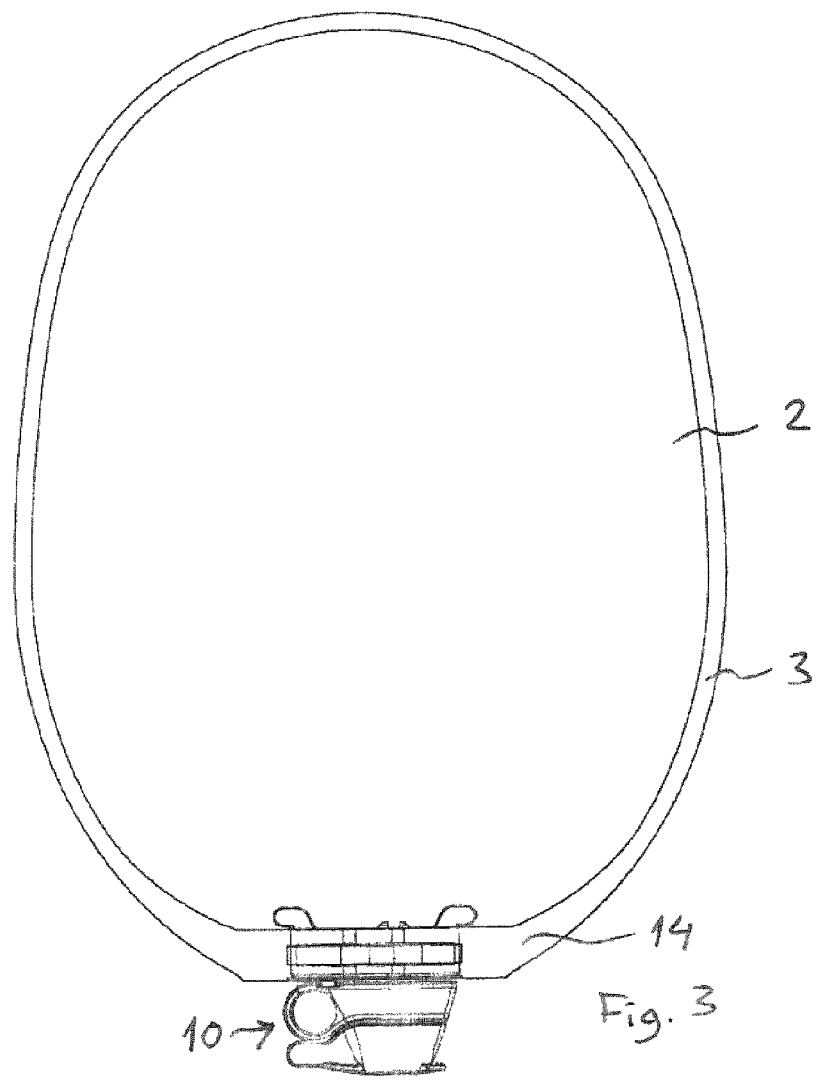
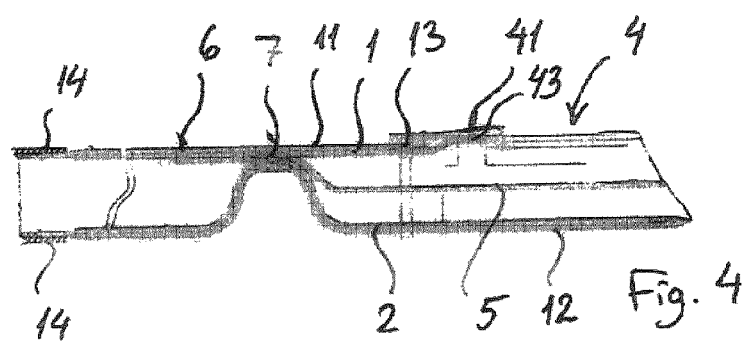

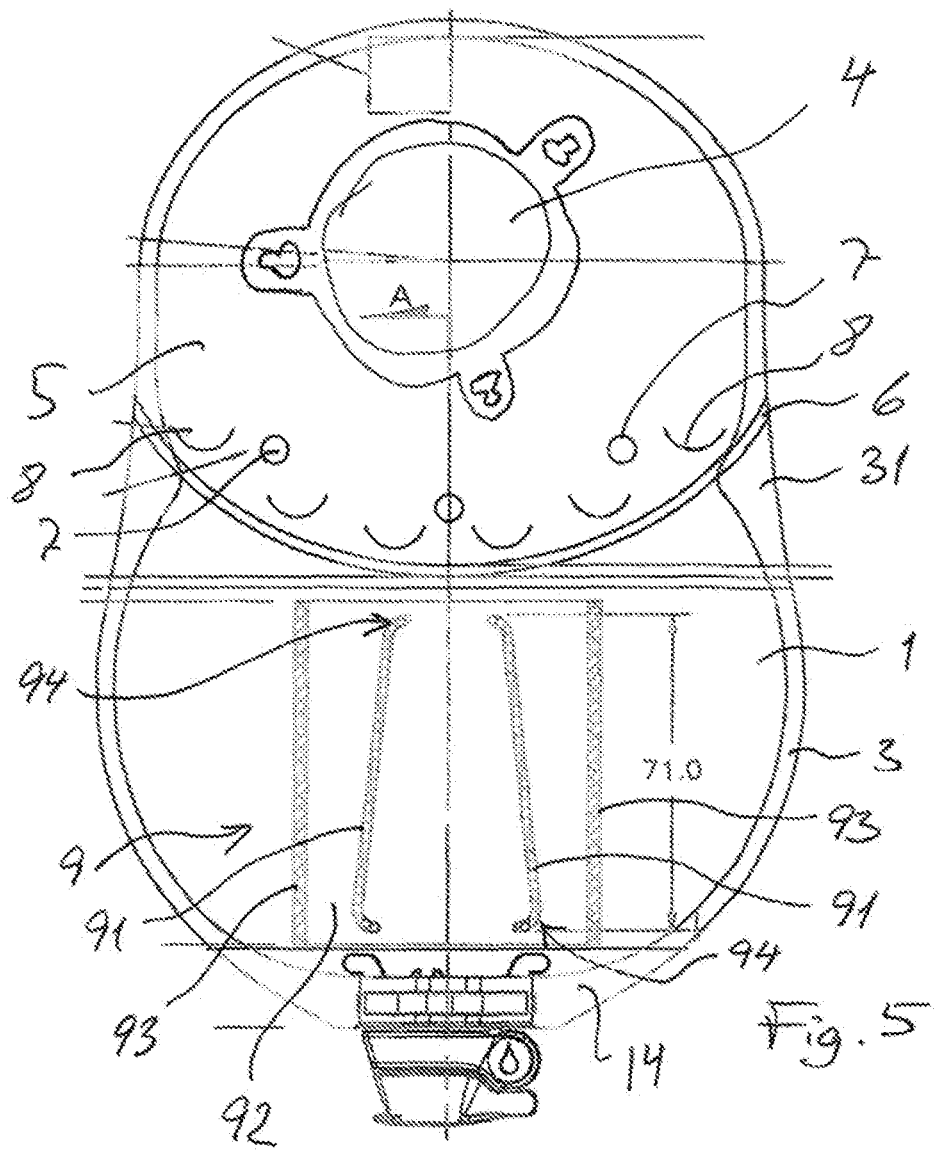
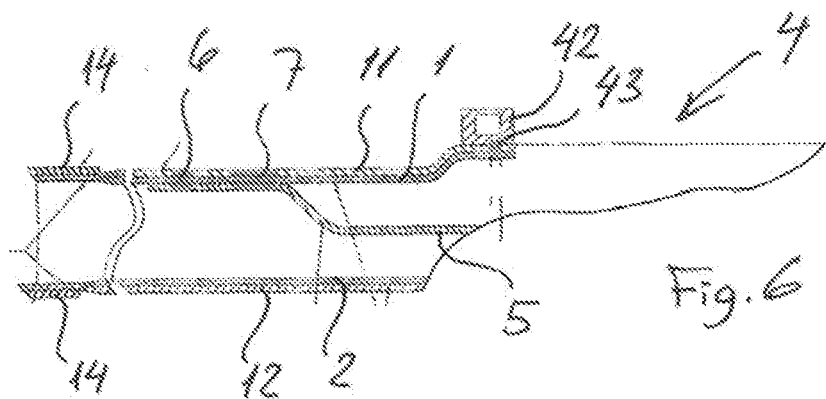

POUCH FOR COLLECTING LIQUID EXCRETIONS

CROSS-REFERENCE TO RELATED APPLICATIONS

This is a National Stage Application of International Patent Application No. PCT/EP2011/069386, filed Nov. 4, 2011, which claims the benefit of and priority to European Patent Application No. 10192174.0, filed Nov. 23, 2010, the contents of which are incorporated fully by reference herein.

BACKGROUND

The present invention relates to a pouch for collecting liquid excretions, such as, for example, a urostomy pouch for collecting liquid human waste, said pouch comprising a first and second wall sealed together along their periphery defining an inlet top portion and a bottom portion defining a collection chamber, an inlet opening provided in the top portion of the first wall, and an anti-reflux film provided in the top portion between said first and second walls.

In order to avoid content from refluxing once it has entered the pouch it is well known to provide a non-return valve in the vicinity of the inlet opening through which urine exits the stoma and enters into the pouch. An example of such arrangement is known from EP 749 507 A2.

Other examples of non-return valve arrangements in urine collection pouches are known from U.S. Pat. No. 4,604,095 and U.S. Pat. No. 4,300,560.

The non-return valve arrangement comprises the provision of intermediate film portions which are attached to each other inside the pouch to form a valve arrangement which is arranged such that liquid is prevented from leaking through the valve arrangement and back towards the inlet opening. Typically, a valve flap is sealed to the first wall of the pouch and another valve flap is sealed adjacently to the second outer wall film of the pouch. The valve flaps may be sealed along their distal lower periphery and a further folded film may be attached to prevent back-flush through the valve. The valve flaps or intermediate walls are also welded to each other at a number of discrete spots linearly arranged across the pouch above the collection chamber where the liquid collects.

The anti-reflux valve arrangement in the pouch takes up a certain volume inside and thereby limits useful volume of the pouch. The urine pouches are designed as drainage bags with a drainage portion at the bottom with a drain valve close the drainage portion which compensates for the limited volume of the collection pouch.

The provision of a non-return valve film arrangement requires subassemblies during manufacture of the pouch prior to assembling the outer walls of the pouch.

SUMMARY OF INVENTION

In accordance with one aspect of the disclosure a pouch is provided for collecting liquid excretions from the human body with an anti-reflux arrangement which is simple in manufacture. In accordance with another aspect of the disclosure a urostomy pouch is provided with increased active volume of the pouch.

The disclosure concerns a pouch for collecting liquid excretions for collecting liquid human waste, said pouch comprising a first and second wall sealed together along their periphery defining an inlet top portion and a bottom portion defining a collection chamber, an inlet opening provided in the top portion of the first wall, and an anti-reflux film provided in the top portion between said first and second walls, wherein the anti-reflux film is sealed along its lower periphery to the first wall by an anti-reflux seal across the first wall, and wherein a plurality of adhesion areas, such as spot welds, are provided above the anti-reflux seal and wherein a plurality of slits are provided in the anti-reflux film between the anti-reflux seal and the adhesion areas.

Hereby, a pouch design is provided which is simple in manufacture. According to a preferred embodiment, the anti-reflux seal being an arcuate seal which is substantially concave relative to the inlet opening and preferably essentially concentric with the inlet opening. Accordingly, the spot welds and the slits are provided in an arcuate configuration in a predetermined distance from arcuate seal. Hereby the active volume for collecting the liquid is increased since the sides of the pouch is included in the active volume due to the concave arcuate sealing of the anti-reflux device.

In a preferred embodiment, the slits are provided with a concave shape with the arcuate portion facing towards the bottom of the pouch. It is also advantageous to provide the slits in an arcuate configuration across the pouch since this allows for an inclination of the bag, e.g. if the user is sitting or lying down. When the pouch is filled to some extent, the concave arcuate shape allow for fluid to flow through more of the slits even when the bag is inclined than if the slits were provided in a straight line across the pouch.

In a preferred embodiment, a drainage portion is provided in the bottom portion of the pouch. Accordingly, the first and second walls are formed with a distal bottom portion to form the drainage portion of the pouch. The drainage portion may be provided with a drain valve which can be operated by the user to empty the pouch. Alternatively, the drainage portion may include a narrow distal portion which is provided with closure means for fold-up closure of the pouch.

In a preferred embodiment of a pouch for collecting liquid excretions according to the disclosure, a baffle member is provided in the collection chamber in the bottom portion of the pouch. This baffle member may preferably comprise a tubular member which is attached to the first and second walls respectively, preferably by a pair of attachment lines, such as heat weldings. Hereby, the liquid content in the pouch is prevented from sloshing and thereby creating discomfort for the user and the bulking out is also restricted.

It is particularly found advantageous that attachment lines are tapered having a wider mutual distance at their lowermost ends than at their uppermost ends and preferably also with an inward bend at the distal ends of the attachment lines to reduce the strains and stresses on the wall in the vicinity of the attachments and thereby preventing any disrupting tear in the pouch walls.

In a preferred embodiment of a pouch according to the disclosure, a non-woven comfort layer is provided on outer side of the first wall. Similarly, a non-woven comfort layer is provided on outer side of the second wall. This is advantageous since the pouch hereby has a soft appearance which makes it more comfortable for the user to wear just as the non-woven layer has a noise-reducing effect so that the pooch is less noisy during use.

BRIEF DESCRIPTION OF THE DRAWINGS

In the following, the invention is described in more detail with reference to the accompanying drawings, in which:

FIG. 1 is body side view of a pouch according to a first embodiment of the disclosure;

FIG. 2 is a horizontal cross-sectional view, taken along lines 2-2 of FIG. 1, through the bottom portion of the pouch in FIG. 1;

FIG. 3 is a distal side view of the pouch of FIG. 1;

FIG. 4 is a detailed vertical cross-sectional view, taken along lines 4-4 of FIG. 1, through the top section of the pouch of FIG. 1;

FIG. 5 is a body side view of a pouch according to a second embodiment of the disclosure; and FIG. 6 is a detailed vertical cross-sectional view, taken along lines 6-6 of FIG. 5, through the top section of the pouch of FIG. 5.

DETAILED DESCRIPTION

With reference to FIGS. 1 to 4, a first embodiment of a pouch for collecting liquid excretions according to the disclosure is shown. The pouch comprises a body-side first wall 1 and a distal second wall 2 which are sealed along their periphery 3 to form the pouch. In the top section 20 of the pouch, an inlet opening 4 is provided in the first wall 1. An intermediate anti-reflux film 5 is provided in the top section 20 between the first and second walls 1, 2. The anti-reflux film 5 may be sealed to the first wall 1 at its lower periphery 6 and to the first and second walls 1, 2 at their common periphery. The anti-reflux film 5 covers the opening 4 and the lower seal 6 is provided a certain distance from the opening 4. The lower seal 6 is preferably provided substantially concentric with the inlet opening 4, i.e. the seal 6 expands across the pouch with a concave shape. A number of adhesion areas, such as spot welds 7, are provided in a similar concave arcuate configuration across the pouch and preferably the spot welds 7 are in the same distance above the anti-reflux seal 6. Between the arcuate seal 6 and the spot welds 7 a plurality of slits 8 are provided in the anti-reflux film 5. The spot welds 7 seal the anti-reflux film 5 to at least the bodyside first wall 1 (as it is the case in the embodiment of FIG. 6), but may also seal to the distal second wall 2 of the pouch as shown in FIG. 4. When adhering both pouch walls 1, 2 and the anti-reflux film 5 the pouch bulging is limited when the pouch is filled with liquid.

By this construction, a collection chamber for storing the liquid content entering the pouch through the opening is provided below the anti-reflux seal 6 as well as between the anti-reflux film 5 and the second wall 2. In the lower section 30 of the pouch a baffle member 9 is provided inside the collection chamber, i.e. between the first and second walls 1, 2 (see FIG. 2).

At the bottom the pouch may be terminated with a drainage valve 10 which is operable by the user for emptying the liquid collected in the pouch. In the drainage portion at the distal lower end of the pouch a reinforcing tape 14 may preferably be applied to both sides of the pouch.

The baffle member 9 may be a tubular structure made up by two sheets of film 92 which are joined together by two longitudinal weldings 93. The tubular structure may be provided with a vertical orientation. The tubular baffle member 9 is attached to the first and second walls 1, 2, respectively. These attachments may be in the form of attachment lines 91 extending in a generally axial direction. Preferably the baffle member 9 is attached to each of the pouch walls 1, 2 by two attachment lines 91 which are generally linear and non-parallel with a wider distance at the lowermost ends than at the uppermost ends. In the embodiments shown in the figures, the two attachment lines 91 on each of the walls 1 and 2 are symmetric around the longitudinal centre line of the pouch and the two pairs of attachments 91, i.e. the two attachment lines 91 joining the baffle member 9 and the first wall 1 and the two attachments 91 joining the baffle member 9 and the second wall 2 are identical in shape and position. The film 92 may be made of a Laminate of different thermoplastic material with a higher melting point on the sides facing the inside of the baffle than the sides of film 92 facing the pouch walls to ensure that the welding during manufacture does not go all the way through. In a preferred embodiment, the material used for the film 92 is a laminate of polypropylene on the inside and polyethylene on the outside of the film 92. In this configuration, the polyethylene on the sides of the film 92 facing the inner sides of the pouch walls 1, 2 has a melting point of approx. 110° C. whereas the polypropylene on the sides of the baffle film 92 forming the inner surfaces of the baffle member 9 has a melting point of about 130-140° C.

In FIG. 4, a schematic cross-section view of the non-return valve arrangement of the pouch of FIGS. 1-3 is shown. The pouch may be attached to the user via coupling means, such as an adhesive wafer 41 which is welded or otherwise fixed to the pouch by the seal 43. The pouch is made up by the bodyside wall 1 and the distal side wall 2 where between an anti-reflux film 5 is arranged in the area around the opening 4. On the outer surfaces of the first wall 1 and the second wall 2, non-woven layers 11, 12, respectively, may be provided for the provision of a comfortable pouch with a soft exterior and which reduces noise from the pouch when the user moves. The comfort layer may be sealed to the first wall 1 around the opening 4 by an annular seal 13. The layers of film, i.e. the exterior comfort layers if, 12, the first and second walls 1, 2 and the intermediate anti-reflux film 5 are joined together at discrete spot welds 7. The position of the arcuate seal 6 of the anti-reflux film 5 to the first wall 1 relative to the spot welds 7 is also'shown in FIG. 4.

Liquid excretions enter into the pouch through the opening 4 and into inlet chamber defined by the first wall 1 and the anti-reflux film 5 in the upper section of the pouch. The liquid will then flow between the wall 1 and the anti-reflux film 5 and pass the spot welds 7 towards the anti-reflux seal 6. Here, the liquid will pass through the slits 6 (see FIG. 1) whereby the liquid enters the collection chamber defined in the lower section of the pouch between the first and second walls 1, 2 and in the upper section of the pouch between the anti-reflux film 5 and second wall 2.

With reference to FIGS. 5 and 6 a second embodiment of a pouch according to the disclosure is shown. The pouch is similar in its design as in the previously described embodiment, i.e. with a body-side first wall and a distal second wall 2 which are sealed along their periphery 3 to form the pouch. In the top section of the pouch, an inlet opening 4 is provided in the first wall 1. An intermediate anti-reflux film 5 may be provided in the top section between the first and second walls 1, 2. The anti-reflux film 5 may be sealed to the first wall 1 at its lower periphery 6 and to the first and second walls 1, 2 at their common periphery. The anti-reflux film 5 covers the opening 4 and the lower seal 6 is provided a certain distance from the opening 4. The lower seal 6 is preferably provided substantially concentric with the inlet opening 4, i.e. the seal 6 expands across the pouch with a concave shape. A number of spot welds 7 are provided in a similar concave arcuate configuration across the pouch and preferably the spot welds 7 are in the same distance above the anti-reflux seal 6. Between the arcuate seal 6 and the spot welds 7 a plurality of slits 8 are provided in the anti-reflux film 5. The spot welds 7 seal the anti-reflux film 5 to the bodyside first wall 1. This is advantageous since the amount of active volume in the collection chamber is increased. However, since this may involve the risk that the pouch bulges when being filled with liquid whereby the pouch may become more visible on the user, the peripheral seal 3 may be provided with inwardly protruding widened heat seal portions 31 to ensure a relative flat configuration of the pouch when being filled during use. The pouch may in this embodiment be attached to the user via mechanical coupling means, such as a coupling ring 42, which is welded or otherwise fixed to the pouch by the seal 43.

The slits 8 in both the shown embodiments are provided with an arcuate profile concave relative to the top of the pouch. Hereby, the slits 8 are opened by fluid flowing from the opening 4 towards the lower section 30 of the pouch. However, liquid already present in the collection chamber in the lower section 30 will prevent the slits 8 from opening whereby the non-return valve effect is achieved.

It is also advantageous to provide the slits 8 in an arcuate configuration across the pouch since this allows for an inclination of the pouch, e.g. if the user is sitting or lying down. When the pouch is filled to some extent, the concave arcuate configuration allows for fluid to flow through more of the slits 8 even when the bag is inclined than if the slits 8 were provided in a straight line across the pouch. Thus, the useful volume when the pouch is inclined is increased.

In relation to the description above of the present disclosure and in the following claims terms like top, bottom, horizontal, vertical and the like are used to describe the construction of the pouch for collecting liquid excretions. These terms are merely to be understood as relative terms and used in order to facilitate the explanation of the pouch construction. Accordingly, it is realised the pouch can be oriented in different directions without departing from the scope of the invention as defined in the claims and that the directional terms are merely to be understood in a relative context.

The invention claimed is:

1. A pouch for collecting liquid excretions for collecting liquid human waste, said pouch comprising
   a first and second wall sealed together along their periphery defining an inlet top portion and a bottom portion defining a collection chamber,
   an inlet opening provided in the top portion of the first wall, and
   an anti-reflux film provided in the top portion between said first and second walls, wherein the anti-reflux film is sealed along its lower periphery to the first wall by an anti-reflux seal across the first wall and sealed to the first and second walls at their common periphery, and wherein a plurality of adhesion areas are provided above the anti-reflux seal and wherein a plurality of slits are provided in the anti-reflux film between the anti-reflux seal and the adhesion areas, wherein the plurality of slits are arranged in an arcuate configuration across the anti-reflux film.

2. A pouch for collecting liquid excretions according to claim 1, wherein said anti-reflux seal being an arcuate seal which is substantially concave relative to the inlet opening and essentially concentric with the inlet opening.

3. A pouch for collecting liquid excretions according to claim 1, wherein the adhesion areas are provided in an arcuate configuration.

4. A pouch for collecting liquid excretions according to claim 1, wherein the slits are provided with a concave shape with the arcuate portion facing towards the bottom of the pouch.

5. A pouch for collecting liquid excretions according to claim 1, wherein a drainage portion is provided in the bottom portion of the pouch.

6. A pouch for collecting liquid excretions according claim 1, wherein a baffle member is provided in the collection chamber in the bottom portion of the pouch.

7. A pouch for collecting liquid excretions according to claim 6, wherein said baffle member comprises a tubular member which is attached to the first and second walls respectively by a pair of attachment lines.

8. A pouch for collecting liquid excretions according to claim 7, wherein said attachment lines are heat weldings.

9. A pouch for collecting liquid excretions according to claim 7, wherein said attachment lines are tapered having a wider mutual distance at their lowermost ends than at their uppermost ends.

10. A pouch for collecting liquid excretions according to claim 7, wherein said tubular baffle member is made of two sheets of thermoplastic film which are sealed together.

11. A pouch for collecting liquid excretions according to claim 10, wherein the two sheets of thermoplastic film of the tubular baffle member is a laminate of different materials, whereby the baffle sheets have a lower melting point on the sides facing the pouch walls than the melting point of the sides facing each other.

12. A pouch for collecting liquid excretions according to claim 1, wherein the adhesion areas are spot welds.

13. A method of manufacturing the pouch for collecting liquid excretions of claim 1, comprising the steps of:
    providing the first wall of the pouch,
    providing the inlet opening in the top portion of said first wall,
    providing the anti-reflux film and sealing said film to the first wall at least along an arcuate lower section in such a manner that the anti-reflux film covers the top portion including the inlet opening of the first wall,
    providing the second wall which is substantially congruent in form and
    sealing said second wall along its periphery to the first wall in such a manner that the anti-reflux film is sandwiched between the first and second walls.

14. A method according to claim 13, wherein the anti-reflux film is provided with slits provided with a concave shape relative to the inlet opening of the pouch with the arcuate portion facing towards the bottom of the pouch.

15. A method according to claim 13, whereby adhesion areas are provided in an arcuate profile between the slits and the arcuate seal adhering at least the anti-reflux film and the first wall.

16. A method according to claim 15, whereby the adhesion areas are spot weldings.

17. A method according to claim 13, wherein the pouch is provided with a drainage portion with a drainage valve in the distal end thereof.

18. A method according to claim 13, wherein a baffle member is provided in the collection chamber in the bottom portion of the pouch.

19. A method according to claim 18, wherein said baffle member comprises a tubular member which is attached to the first and second walls respectively by a pair of attachment lines.

20. A method according to claim 18, wherein said attachment lines are tapered having a wider mutual distance at their lowermost ends than at their uppermost ends.

21. A method according to claim 18, wherein said tubular baffle member is made of two sheets of thermoplastic film which are sealed together.

22. A method according to claim 16, wherein a non-woven comfort layer is provided on outer side of the first wall before sealing to the anti-reflux film on the inner side of the first wall.

23. A method according to claim 16, wherein a non-woven comfort layer is provided on outer side of the second wall before or simultaneous with sealing the second wall to the first wall and to the anti-reflux film.

24. A method according to claim 16, wherein said anti-reflux seal being an arcuate seal which is substantially concave relative to the inlet opening and essentially concentric with the inlet opening.

* * * * *

UNITED STATES PATENT AND TRADEMARK OFFICE
CERTIFICATE OF CORRECTION

PATENT NO. : 9,119,727 B2
APPLICATION NO. : 13/988235
DATED : September 1, 2015
INVENTOR(S) : Hannan et al.

It is certified that error appears in the above-identified patent and that said Letters Patent is hereby corrected as shown below:

In the Specification

Column 1, line 27, delete "EP 749" and insert --EP 1 749--.

Column 2, line 59, delete "pooch" and insert --pouch--.

Column 4, line 3, delete "Laminate" and insert --laminate--.

Column 4, line 28, delete "if," and insert --11,--.

Column 4, line 32, delete "also'" and insert --also--.

Column 4, line 38, delete "6" and insert --8--.

Column 4, line 46, delete "wall" and insert --wall 1--.

In the Claims

Column 5, line 65, Claim 6, delete "according claim" and insert --according to claim--.

Signed and Sealed this
Sixteenth Day of August, 2016

Michelle K. Lee
*Director of the United States Patent and Trademark Office*